(12) United States Patent
Greep et al.

(10) Patent No.: US 11,617,611 B2
(45) Date of Patent: Apr. 4, 2023

(54) HAND-HELD INSTRUMENT WITH DUAL ZONE FLUID REMOVAL

(71) Applicant: Megadyne Medical Products, Inc., Draper, UT (US)

(72) Inventors: Darcy W. Greep, Herriman, UT (US); Chad S. Frampton, American Fork, UT (US)

(73) Assignee: Megadayne Medical Products, Inc., Draper, UT (US)

( * ) Notice: Subject to any disclaimer, the term of this patent is extended or adjusted under 35 U.S.C. 154(b) by 350 days.

(21) Appl. No.: 15/599,273

(22) Filed: May 18, 2017

(65) Prior Publication Data

US 2017/0360499 A1    Dec. 21, 2017

Related U.S. Application Data

(60) Provisional application No. 62/351,811, filed on Jun. 17, 2016.

(51) Int. Cl.
*A61B 18/00* (2006.01)
*A61B 18/14* (2006.01)
*A61B 17/00* (2006.01)

(52) U.S. Cl.
CPC ............ *A61B 18/1402* (2013.01); *A61B 2017/00424* (2013.01); *A61B 2018/00589* (2013.01); *A61B 2018/00601* (2013.01); *A61B 2018/00607* (2013.01); *A61B 2018/00708* (2013.01); *A61B 2018/00922* (2013.01);
(Continued)

(58) Field of Classification Search
CPC ........ A61B 2218/006; A61B 2218/008; A61B 17/00; A61B 18/12; A61B 18/14; A61B 18/18; A61B 18/402; A61B 2018/00589; A61B 2018/00607; A61B 2018/00708; A61B 2018/00922; A61B 2018/00958; A61B 2018/1475; A61B 2017/00424; A61B 1/00094; A61B 1/012; A61B 1/015; A61B 1/12; A61B 1/126; A61B 1/127; A61B 1/303; A61B 1/317; A61B 2218/001; A61B 2218/002; A61B 2218/007; A61B 2017/32007; A61B 2018/0035

See application file for complete search history.

(56) References Cited

U.S. PATENT DOCUMENTS

4,719,914 A * 1/1988 Johnson ............... A61B 18/082
604/35
4,850,352 A * 7/1989 Johnson ............... A61B 18/082
606/13
(Continued)

*Primary Examiner* — Joanne M Rodden
*Assistant Examiner* — Rachel A. Vierra
(74) *Attorney, Agent, or Firm* — Workman Nydegger (57) ABSTRACT

An electrosurgical instrument has dual zone smoke evacuation for providing efficient capture and evacuation of smoke generated during an electrosurgical procedure. A hand piece with a proximal and a distal end is coupled to a front piece having a distal opening leading into an interior conduit. An extendable section is at least partially disposed within the interior conduit and extends distally out of the distal opening of the front piece. The extendable section is selectively translatable within the interior conduit. A negative pressure source enables the capture and evacuation of smoke through both the extendable section and the interior conduit.

31 Claims, 4 Drawing Sheets

(52) U.S. Cl.
CPC .............. *A61B 2018/00958* (2013.01); *A61B 2018/1475* (2013.01); *A61B 2218/008* (2013.01)

(56) References Cited

U.S. PATENT DOCUMENTS

| | | | | |
|---|---|---|---|---|
| 5,234,428 | A * | 8/1993 | Kaufman | A61B 18/1402 604/35 |
| 5,265,840 | A * | 11/1993 | Gillespie | A61M 1/7413 251/7 |
| 6,099,525 | A * | 8/2000 | Cosmescu | A61B 18/00 604/35 |
| 6,146,353 | A * | 11/2000 | Platt, Jr. | A61B 18/00 604/22 |
| 6,458,125 | B1 * | 10/2002 | Cosmescu | A61B 18/042 606/41 |
| 7,500,974 | B2 * | 3/2009 | Sartor | A61B 18/1402 606/45 |
| 9,101,363 | B2 * | 8/2015 | Zinnanti | A61B 18/14 |
| 10,405,917 | B2 * | 9/2019 | Shvetsov | A61B 18/1477 |
| 2002/0103485 | A1 * | 8/2002 | Melnyk | A61B 18/14 606/45 |
| 2004/0034339 | A1 * | 2/2004 | Stoller | A61B 1/3132 606/1 |
| 2007/0129722 | A1 * | 6/2007 | Cosmescu | A61M 39/1055 606/42 |
| 2009/0018539 | A1 * | 1/2009 | Cosmescu | A61M 39/1055 606/41 |
| 2009/0062791 | A1 * | 3/2009 | Lee | A61B 18/1402 606/45 |
| 2010/0160911 | A1 | 6/2010 | Ducharme | |
| 2012/0203165 | A1 * | 8/2012 | Terry | A61B 18/1402 604/35 |
| 2012/0283728 | A1 * | 11/2012 | Cosmescu | A61B 18/1477 606/46 |
| 2014/0257273 | A1 * | 9/2014 | Cosmescu | A61B 18/042 606/37 |
| 2014/0276763 | A1 * | 9/2014 | Greep | A61B 18/1402 606/34 |
| 2015/0005761 | A1 * | 1/2015 | Zinnanti | A61B 18/1482 606/37 |
| 2015/0112323 | A1 * | 4/2015 | Hagg | A61B 18/1206 606/34 |
| 2015/0209100 | A1 * | 7/2015 | Ineson | A61B 18/1402 606/42 |
| 2015/0335376 | A1 * | 11/2015 | Hufnagel | A61B 18/1402 606/39 |
| 2016/0206361 | A1 * | 7/2016 | Jadhav | A61B 18/08 |
| 2018/0028255 | A1 * | 2/2018 | Miller | A61B 18/12 |

* cited by examiner

HAND-HELD INSTRUMENT WITH DUAL ZONE FLUID REMOVAL

This application claims priority to and the benefit of U.S. Provisional Patent Application No. 62/351,811, filed Jun. 17, 2016, and entitled HAND-HELD INSTRUMENT WITH DUAL ZONE FLUID REMOVAL, the entirety of which in incorporated herein.

BACKGROUND

1. Technical Field

This disclosure relates to hand-held instruments. More particularly, the disclosure relates to fluid removal components of hand-held instruments.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument.

When an electrosurgical instrument is used for cutting or coagulation, smoke is commonly produced. A surgeon or assistant often uses a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, combination electrosurgical instrument and smoke evacuation devices have been developed. These combination devices often include a hand piece that can receive an electrode or tip in a distal end thereof for performing electrosurgical procedures. The hand piece is connected to a generator via a power cable to convey RF current to the electrode or tip. Additionally, a smoke evacuation hose is connected between the hand piece and a vacuum to draw smoke away from the surgical site.

Although such combination electrosurgical instrument and smoke evacuation devices typically evacuate some of the smoke produced during an electrosurgical procedure, some amount of smoke may not be fully captured by the smoke evacuation hose. In some instances, the amount of non-evacuated smoke is substantial, leading to reduced visibility at the surgery area as well as to unpleasant odors at the surgery location. Excessive amounts of smoke produced during electrosurgery can also irritate the eyes and respiratory tissues of those in the surgery area, an undesirable effect in situations where the focus and concentration of the surgeon/operator and any assistants is paramount. Further, non-evacuated smoke can leave an unpleasant odor on nearby clothes, equipment, and other items, even after an electrosurgical procedure is completed. Additionally, surgical smoke produced by electrosurgical, laser, or other methods has been found to contain harmful, even carcinogenic chemicals and materials which can present a danger to operating room personnel, surgeons, and patients who may inhale the smoke. Virus particles have also been isolated from surgical smoke and there is increasing evidence that certain viral strains have actually been inhaled through electrosurgical smoke by surgeons, resulting in lesions in their airways.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present disclosure relates to electrosurgical instruments and other hand-held instruments having dual zone fluid evacuation functionality. In some embodiments, the hand-held instrument is an electrosurgical instrument having a dual zone fluid evacuation assembly configured to efficiently remove smoke generated during an electrosurgical procedure. In some embodiments, an electrosurgical instrument includes a first smoke evacuation component and a second smoke evacuation component, the first smoke evacuation component being disposed at a distal portion of the electrosurgical instrument and the second smoke evacuation component being disposed proximal of the first smoke evacuation component.

One or more embodiments beneficially enable the capture and evacuation of smoke generated during an electrosurgical procedure. In particular, smoke which is generated near the first smoke evacuation component but which is not captured by the first smoke evacuation component can be captured by the second smoke evacuation component. Beneficially, such electrosurgical instruments having a dual zone smoke evacuation assembly can enable greater capture of smoke generated in an electrosurgical procedure, reducing the amount of smoke available for reducing visibility, irritating operators and/or assistants, causing odors, and/or limiting the effectiveness of an electrosurgical procedure in other ways.

Reference is made herein to the evacuation of smoke and components that facilitate such function. It will be appreciated that references to "smoke" is merely for simplicity and convenience, and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site.

Figure 1:
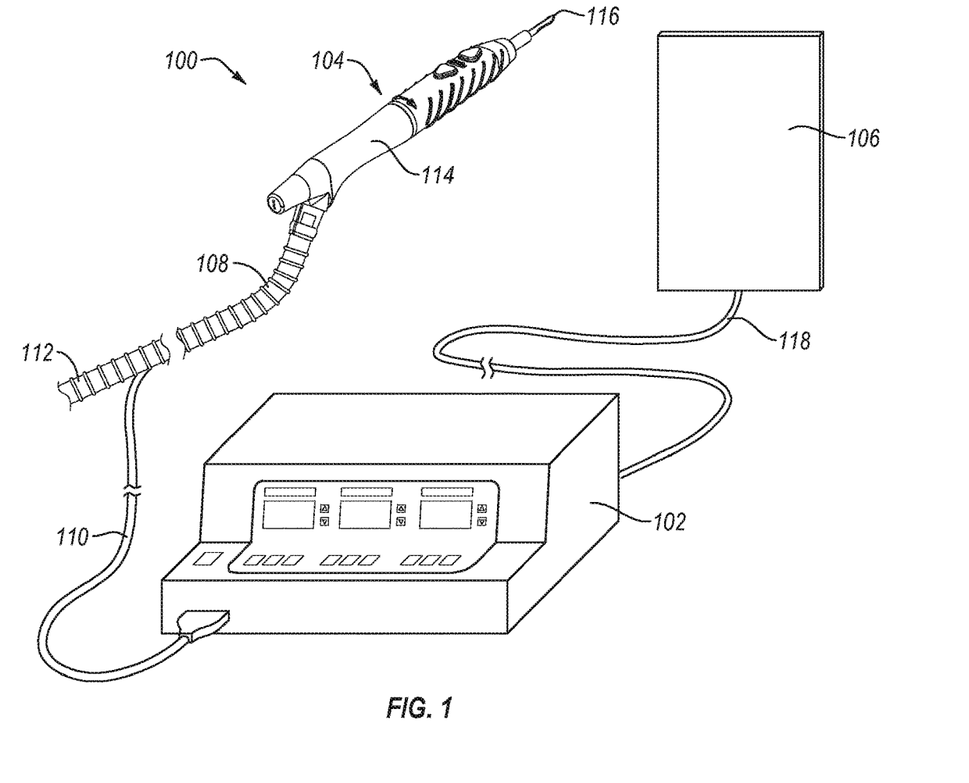
FIG. 1 illustrates an exemplary electrosurgical system.

FIG. 1 illustrates an exemplary electrosurgical system 100. The illustrated embodiment includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site. In some embodiments, such as that illustrated in FIG. 1, cable 110 can extend through at least a portion of vacuum hose 112.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Return electrode 106 is connected to generator 102 by a cable 118 in order to complete the circuit and provide a return electrical path to wave generator 102 for energy that passes into the patient's body.

As explained in greater detail below, embodiments of electrosurgical instruments according to the present disclosure enable efficient capture of smoke generated during an electrosurgical procedure, such that smoke that is not immediately captured near the site of smoke generation (e.g., at the tissue/electrode tip interface) can still be captured and evacuated away from the operating environment.

Figure 2:
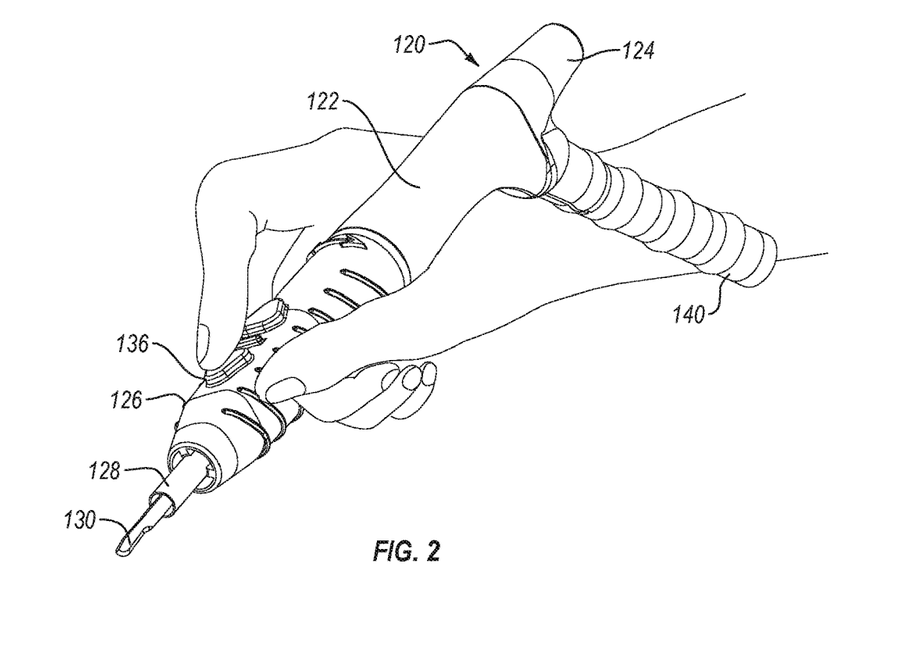
FIG. 2 illustrates an electrosurgical instrument as held by an operator.

Illustrated in FIG. 2 is an exemplary electrosurgical instrument 120 used to perform electrosurgical procedures and evacuate smoke from a surgical site. Electrosurgical instrument 120 includes a hand piece 122 having a proximal end 124 and a distal end 126. An extendable section 128 is selectively extendable (e.g., translatable along an axis running in the proximal/distal direction) and includes a channel or conduit extending therethrough. An electrode tip 130 is received within the distal end of the extendable section 128. One or more power cables, one or more vacuum hoses, and/or other connections can be directed to the hand piece 122 through the utility conduit 140, which in the illustrated embodiment, is coupled to the hand piece 122 near the proximal end 124 and on an underside of the hand piece 122. Alternative embodiments can include utility conduit connections on a top and/or side section of a hand piece, at the proximal end extending proximally, or at other locations of the hand piece. The power cable communicates electrical energy from an electrosurgical generator to electrosurgical instrument 120. During an electrosurgical procedure, the electrical energy is passed through electrode tip 130 and into a patient's tissue.

Electrosurgical instruments, such as electrosurgical instrument 120, are commonly referred to as electrosurgical pencils or pens because in use they are often held in the same manner that a pencil or pen is held when writing. FIG. 2 illustrates a common manner by which an operator can hold an electrosurgical instrument during an electrosurgical procedure. As shown, hand piece 122 is laid through the crook of the hand and is held in place by the middle finger and thumb. The index finger can be placed on top of hand piece 122 to further hold hand piece 122 in place as well as to control certain actions of the electrosurgical device through selective activation of one or more controls 136.

Figure 3:
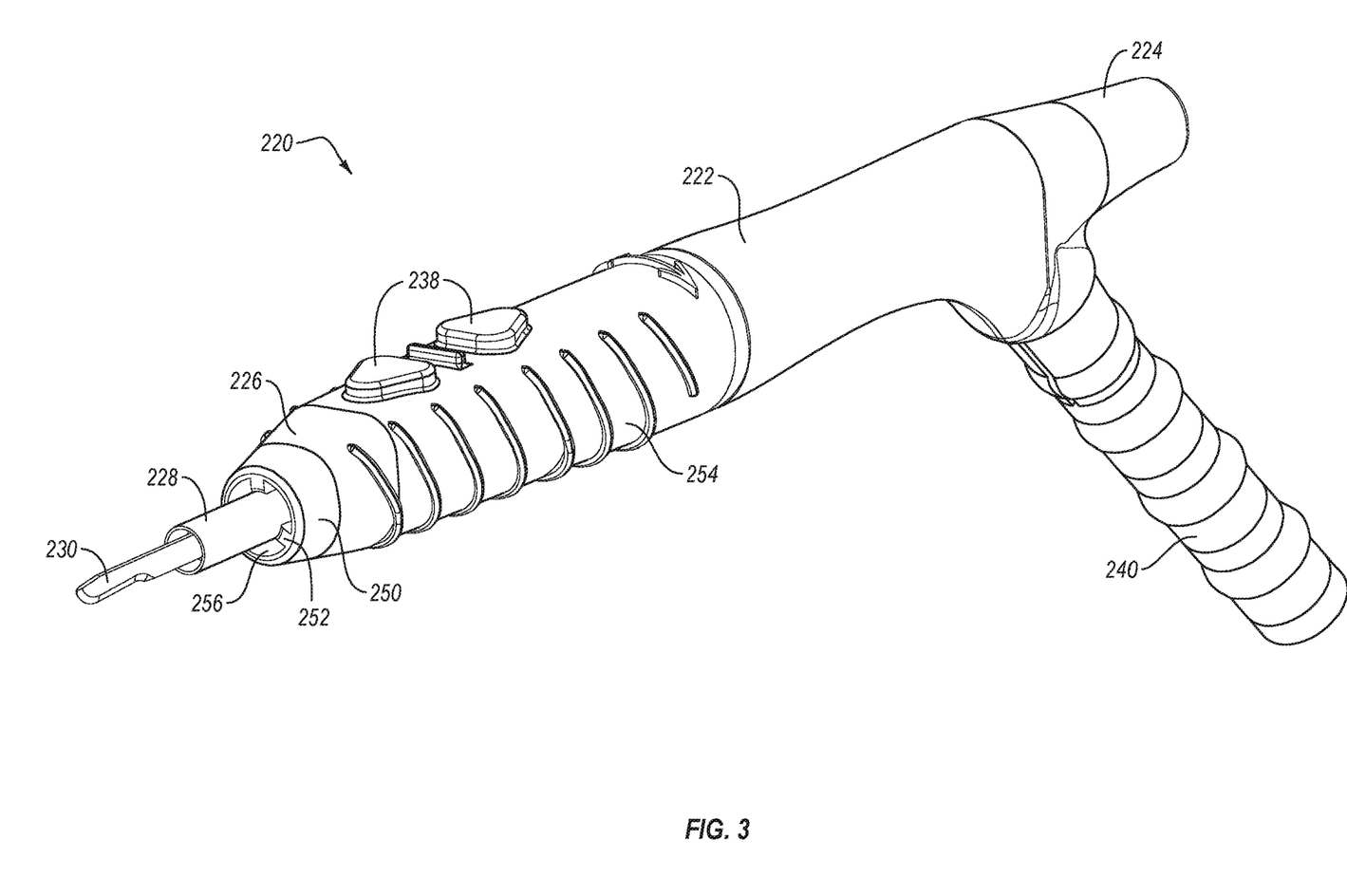
FIG. 3 illustrates an electrosurgical instrument having a dual zone smoke evacuation assembly.

FIG. 3 illustrates an embodiment of an electrosurgical instrument 220 configured with dual zone smoke evacuation. The illustrated embodiment includes a hand piece 222 having a proximal end 224 and a distal end 226. An extendable section 228 is disposed at least partially within the interior of the hand piece 222 and extends distally out of the hand piece 222. The extendable section 228 is configured to receive an electrode tip 230. In some embodiments, the extendable section 228 is formed from a conductive material and is configured to pass electrical current from a power cable (e.g., a power cable disposed within the illustrated utility conduit 240) to the electrode tip 230.

The extendable section 228 is preferably configured as a conduit (e.g., tube or other shape having a hollow or partially hollow cross-section). The conduit of the extendable section 228 is configured to pass at least partially into an internal chamber of the hand piece 222 and to be in fluid communication with the utility conduit 240 (and/or with a vacuum hose attached/disposed in the utility conduit 240). The extendable section 228 also includes a distal end opening providing fluid communication between the interior of the extendable section and the atmosphere exterior to the extendable section 228. As shown, the electrode tip 230 can be coupled to the extendable section 228 (e.g., via adhesive, welding, mechanical fastening, notches, slots, and/or friction fitting, or through integral formation of a single piece) in a manner that leaves one or more aperture spaces for smoke capture into the interior of the extendable section 228.

The illustrated embodiment can also include a front piece 250 having an opening for the extendable section 228 to pass through. In this embodiment, the front piece 250 is formed with a tapered profile that tapers inwardly in the distal direction. In other embodiments, the front piece 250 is formed without a tapered shape (e.g., a squared or straight edge profile), or with a different taper or curved profile.

The illustrated front piece 250 includes one or more supports 252 configured to hold or stabilize the extendable section 228 in position with respect to the front piece 250 (e.g., in the illustrated coaxial position with an interior conduit of the hand piece 222). The one or more supports 252 can be configured to frictionally maintain the position of the extendable section 228. For example, the one or more supports 252 can be configured to allow a user to adjust the extendable section 228 when desired, while otherwise maintaining the position of the extendable section 228 during normal operation of the instrument (e.g., securing against movement caused by gravity or other relatively minor forces).

The illustrated front piece 250 includes supports 252 formed as radial extensions. Other embodiments can include one or more legs, braces, helical extrusions, and/or other support structures. As shown, the front piece 250 includes an opening 256 to enable fluid communication between the atmosphere exterior to the hand piece 222 and the interior of the hand piece 222.

The embodiment shown in FIG. 3 also includes a grip 254 configured to provide a tactile surface for a user to hold and/or control the electrosurgical instrument 220. The grip 254 can be formed from a rubber or polymer material, for example, and can include one or more ridges, grooves, and/or other surface features for providing comfort and/or tactile gripping enhancement to a user while holding the instrument.

The illustrated embodiment also includes one or more controls 238 enabling a user to adjust one or more parameters of the electrosurgical instrument 220, such as increasing or decreasing electrical power delivery through the instrument, turning the instrument on and off, adjusting the instrument for different operating modes (cut, coagulate, cut-coagulate blend), etc. For example, the controls 238 can provide a connection for transmitting control signals from the electrosurgical instrument 220 to an electrosurgical generator and/or other controller.

Figure 4:
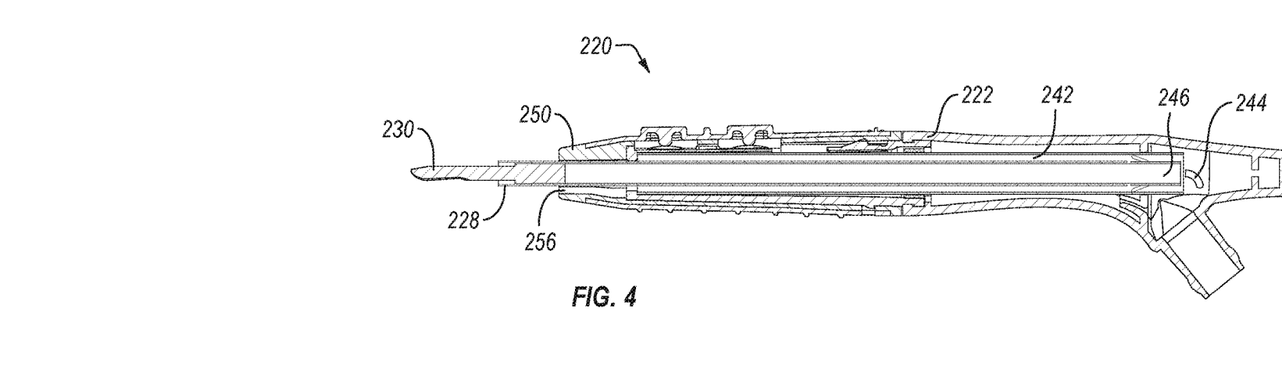
FIG. 4 illustrates a cross-sectional view of the electrosurgical instrument of FIG. 3, showing an extendable section positioned in a retracted position.

FIG. 4 illustrates a cross-sectional view of the electrosurgical instrument 220 shown in FIG. 3. FIG. 4 illustrates the extendable section 228 in a retracted position, showing that much of the extendable section 228 can be positioned within the interior of the hand piece 222. The illustrated embodiment also includes an interior conduit 242 disposed within the interior of the hand piece 222 and configured in size and shape to enclose the extendable section 228 (e.g., at least the portions not extending distally beyond the hand piece 222) so that the extendable section 228 fits within the interior conduit 242 and is selectively translatable within the interior conduit 242. As shown, the interior conduit 242 is in fluid communication with the atmosphere exterior to the hand piece 222 via one or more openings 256 at the front piece 250, enabling the capture of smoke into the interior conduit 242 through the one or more openings 256.

In some embodiments, the electrosurgical instrument 220 includes a back stop 244 positioned to limit proximal translation of the extendable section 228 within the interior conduit 242. For example, the back stop 244 can be disposed at a position such that when the extendable section 228 is fully retracted, the electrode tip 230 is at or near the distal portion of the hand piece 222 but is not retracted into the interior of the hand piece 222.

The illustrated back stop 244 is formed as a crosspiece to prevent proximal movement of the extendable section 228 past the back stop 244. Alternatively, the back stop 244 can be formed as a wall, rib, detent, abutment, catch, brace, and/or other means of preventing relative movement.

The illustrated electrosurgical instrument 220 also includes a connector 246 coupled to the extendable section 228 at the proximal end of the extendable section 228. As shown, the connector 246 has one or more projections extending radially outwardly to the wall of the interior conduit 242. In some embodiments, the one or more projections function as friction fitting components for maintaining the position of the extendable section 228 relative to the interior conduit 242 (e.g., in addition to, or as an alternative to, frictional securement through engagement between the supports 252 and the extendable section 228). For example, the connector 246 can be configured to hold the extendable section 228 in position during normal operation and movement of the electrosurgical instrument 220 (e.g., to hold position against gravity and/or against lighter forces resulting from movement of the hand piece 222) while still allowing user adjustment of the extendable section 228 under directed (e.g., hand-applied) force.

In some embodiments, the connector 246 is electrically conductive and is configured to pass electrical current to the extendable section 228. In some embodiments, the extendable section 228 is also electrically conductive and is able to pass electrical current to the electrode tip 230. For example, a power cable can extend into the interior of the hand piece 222 (e.g., through a utility conduit) to be coupled to the connector 246 and/or extendable section 228. Alternatively, the connector 246 and/or extendable section 228 can be formed of a non-conductive material, and a power cable can extend to the electrode tip 230 or to other intermediate components in order to deliver electrical current to the electrode tip 230. In some embodiments, the extendable section 228 and/or connector 246 may be formed from a conductive material that is at least partially coated with a non-conductive material to prevent the transfer of current from the extendable section 228 to patient tissue during an electrosurgical procedure.

As shown, the extendable section 228 can be formed with a length (measured along the proximal-distal axis) to be about the same length (e.g., within 99% of, 95% of, 90% of, 80% of, or 75%) of the hand piece 222 in which it can selectively translate within. In other embodiments, the extendable section 228 may be shorter or longer, such as about 0.75 times or 0.5 times the length of the hand piece 222, or about 1.25, 1.5, 2, or 2.5 times longer than the length of the hand piece 222.

Figure 5:
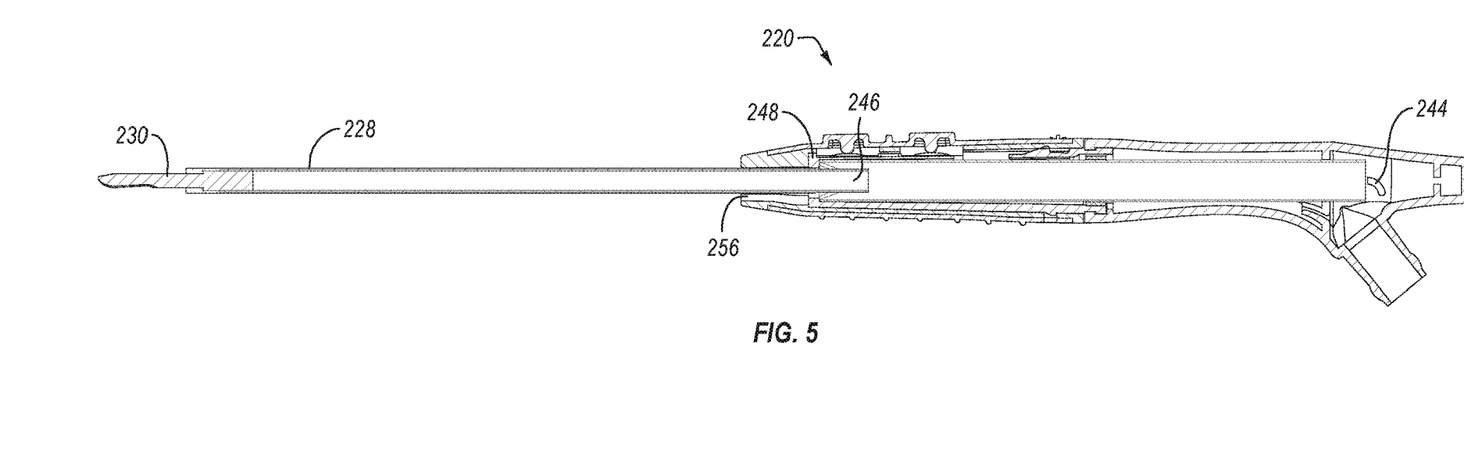
FIG. 5 illustrates a cross-sectional view of the electrosurgical instrument of FIGS. 3 and 4, showing the extendable section positioned in an extended position.

FIG. 5 illustrates the electrosurgical instrument 220 with the extendable section 228 in an extended position. The embodiment shown in FIG. 5 includes a front stop 248 configured to prevent distal movement of the extendable section 228 past the front stop 248. In this embodiment, the front stop 248 is configured as an annular structure having an inner diameter that is smaller than the inner diameter of the interior conduit 242. In this configuration, the extendable section 228 is prevented from passing further distally through the front stop 248 when the connector 246 is brought into contact with the front stop 248. For example, because the projections of the connector 246 extend to the wall of the interior conduit 242, they cannot pass through the smaller diameter of the front stop 248 and thereby limit the distal extension of the extendable section 228.

In other embodiments, movement of the extendable section 228 can be limited in other ways. For example, the extendable section 228 can include a key or keyway matched to a corresponding keyway or key of the hand piece 222 and/or front piece 250, and a track/rail system can be formed to limit translation of the extendable section 228 to a desired range.

In some embodiments, moving the extendable section 228 to the fully extended position, as shown in FIG. 5, may close off or block the one or more openings 256 at the front piece 250. For instance, when the projections of the connector 246 or other components near the proximal end of the extendable section 228 engage the front stop 248, the projections or other components may close off or block the one or more openings 256, thereby preventing capture of smoke through the one or more openings 256. In some instances, closing off or blocking the one or more openings 256 may increase the negative pressure applied through the conduit of the extendable section 228, thereby increasing the amount of smoke captured through the extendable section 228. This negative pressure increase through the conduit of extendable section 228 may be particularly helpful when working in a pocket to increase the airflow into the pocket, thus capturing more smoke through the distal end of extendable section 228.

Figure 6:
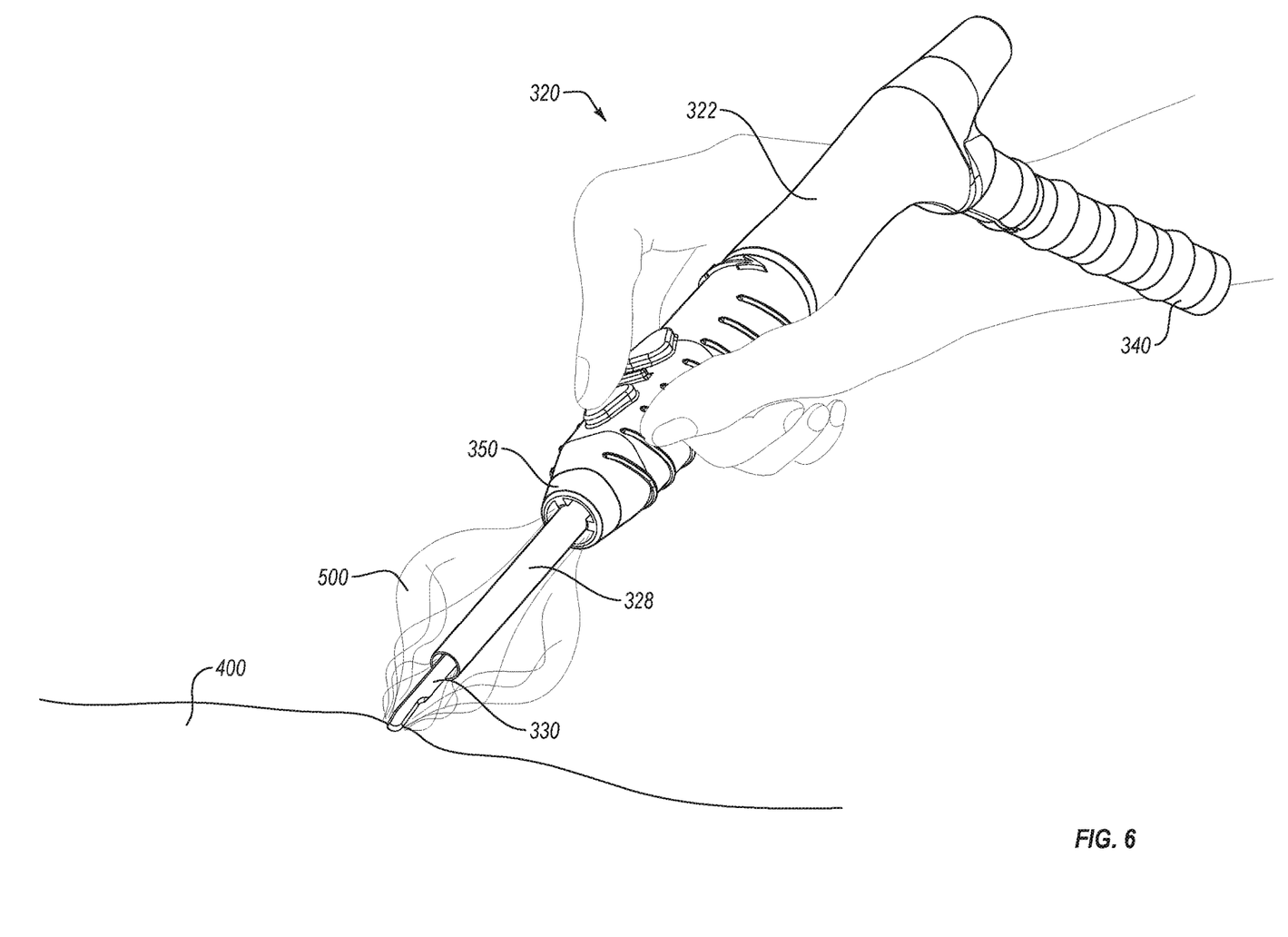
FIG. 6 illustrates an electrosurgical instrument in use, showing efficient smoke evacuation via a dual zone smoke evacuation assembly of the electrosurgical instrument.

FIG. 6 illustrates an embodiment of an electrosurgical instrument 320 being used to treat a target tissue 400 during an electrosurgical procedure. As shown, negative pressure is applied via a vacuum hose, which, in this embodiment is located within a utility conduit 340. The vacuum hose is in fluid communication with the conduit of the extendable section 328 and the interior conduit (not shown in this view). The applied negative pressure enables the extendable section 328 to capture some of the smoke 500 generated in the vicinity of the electrode tip 330 during an electrosurgical procedure. The captured smoke 500 can pass through the conduit of the extendable section 228 and into utility conduit 340. In this manner, the extendable section 328 functions as a first smoke evacuation component.

During an electrosurgical procedure, some of the generated smoke, and in some instances, much of the generated smoke, is dispersed away from the distal opening of the extendable section 328 prior to being captured by and evacuated by the extendable section 328. For example, generated smoke may disperse outwardly from the point of generation near the electrode tip 330 at an angle that prevents a portion of the generated smoke from passing close enough to the distal opening of the extendable section 328 to be captured by the extendable section 328. In addition, some portions of the generated smoke may not be captured by the distal opening of the extendable section 328 when the electrode tip 330 is angled away from the general direction of smoke travel (e.g., when the electrosurgical instrument 320 is positioned so as to put the electrode tip 330 at a low angle relative to the treated tissue). Further, in some instances drafts or other disturbances in the atmosphere of the operating environment may direct generated smoke away from the distal opening of the extendable portion 328, preventing capture of at least a portion of the generated smoke. Additionally, in some instances movement of the electrode tip 330 occurs across the tissue 400 at such a rate that smoke 500 emanating from the treated tissue 400 is not captured prior to movement of the distal opening of the extendable section 328 away from the treated tissue 400, and a portion of smoke 500 escapes capture.

As shown in FIG. 6, the front piece 350 and the interior conduit (not shown in this view) to which it is in fluid communication with function as a second smoke evacuation component. The second smoke evacuation component can beneficially function to capture at least a portion of generated smoke that is not captured by the first smoke evacuation component. The distal opening of the front piece 350 enables the capture of smoke into the interior conduit of the electrosurgical instrument 320. The interior conduit is in fluid communication with the utility conduit 340 (e.g., with a vacuum hose disposed within the utility conduit 340) such that the captured smoke can be evacuated through the utility conduit 340.

In the illustrated embodiment, the first smoke evacuation component (e.g., the extendable section 328) is configured to be selectively translatable relative to the body of the hand piece 322, and the second smoke evacuation component (e.g., the front piece 350 and the interior conduit) is configured to be stationary relative to the body of the hand piece 322. For example, as the extendable section 328 is translated (extended or retracted), the relative position of the first smoke evacuation component with respect to the body of the hand piece 322 is readjusted, while the relative position of the second smoke evacuation component with respect to the body of the hand piece 322 is maintained.

Likewise, the first smoke evacuation component is configured to be stationary relative to the electrode tip 330 while the second smoke evacuation component is configured to be selectively translatable relative to the electrode tip 330. For example, as the extendable section 328 is translated (extended or retracted), the relative position of the first smoke evacuation component with respect to the electrode tip 330 is maintained, while the relative position of the second smoke evacuation component with respect to the electrode tip 330 is readjusted.

In this embodiment, the second smoke evacuation component is positioned proximal to the first smoke evacuation component, enabling the capture of smoke which passes proximally beyond the first smoke evacuation component without capture. In addition, the second smoke evacuation component is configured with a capture diameter that is larger than a capture diameter of the first smoke evacuation component (e.g., the diameter of the distal opening of the front piece 350 is larger than the diameter of the distal opening of the extendable section 328), enabling the capture of smoke which passes outwardly beyond the first smoke evacuation component without capture. In some embodiments, the ratio of the diameter of the distal opening of the front piece 350 to the diameter of the distal opening of the extendable section 328 is about 10:1 to about 1.1:1, or about 3:1 to about 2:1.

Some embodiments described herein include first and second smoke evacuation components having conduits formed with a circular cross-section shape. Alternative embodiments include first and/or second smoke evacuation components having different sizes and/or shapes. For example, the first and/or second smoke evacuation components may have conduits with a rectangular, square, ovoid, polygonal, or other shaped cross-section.

Embodiments described herein can provide a number of benefits. For example, during an electrosurgical procedure, a portion of the generated smoke can be captured by the first smoke evacuation component (e.g., to be channeled through the conduit of an extendable section). At least a portion of the smoke not captured by the first smoke evacuation component, such as smoke that is dispersed proximally and/or outwardly at too great an angle to be directed into the first smoke evacuation component, can then be captured by the second smoke evacuation component.

In addition, the first and second smoke evacuations components are beneficially configured such that for a given reference point, one smoke evacuation component maintains a stationary positional relationship to the reference point while the other smoke evacuation component provides a dynamically adjustable positional relationship. For example, from the perspective of a reference point at the electrode tip 330, the first smoke evacuation component maintains a positional relationship with the electrode tip 330 while the second smoke evacuation component provides an adjustable positional relationship with the electrode tip 330. This can enable greater smoke capture and evacuation. For example, such a configuration allows the second smoke evacuation component to be oriented (e.g., by extending or retracting the extendable portion 328 and/or by angling the hand piece 322) relative to the electrode tip 330 to a position that increases or maximizes capture of dispersed smoke, while at the same time maintaining the first smoke evacuation component near the electrode tip 330 in order to more immediately capture a portion of the generated smoke.

In another example, the illustrated embodiment enables an operator to dynamically adjust the electrosurgical instrument 320 during an electrosurgical procedure to increase the capture and evacuation of generated smoke. For example, an operator may notice that a portion of the generated smoke is being directed away from the treated tissue in a given direction before the first smoke evacuation component can capture it. The operator may reorient the hand piece 322 toward the direction the portion of smoke is traveling so as to increase the amount of that smoke captured by the second smoke evacuation device (e.g., enough to bring the smoke under the influence of the negative pressure zone near the distal opening of the front piece 350).

Additionally, or alternatively, the operator may extend or retract the extendable section 328 in order to adjust the positional relationship between the electrode tip 330 and the second smoke evacuation component. For example, the operator may notice that a portion of the generated smoke not captured by the first smoke evacuation component is dispersing in such a way that capture could be increased by retracing or extending the extendable section 328 in order to bring the second smoke evacuation component closer to or farther from the electrode tip 330.

Further, one or more embodiments described herein can beneficially reduce or eliminate the amount of generated smoke passing to the operating environment without capture, thereby reducing the visibility reduction, odor, and other problems associated with smoke generation. In some instances this can enable electrosurgical procedures that generate greater amounts of smoke to be performed or to be performed with less ancillary equipment (e.g., less additional independent vacuum hoses, fans, and other air management equipment).

One or more embodiments described herein can also enable an electrosurgical instrument to have an extendable section with a smaller diameter. For example, because smoke not captured by the extendable section can be captured and evacuated by a second smoke evacuation component, the size and shape of the extendable section need not be limited by its smoke evacuation ability.

While the embodiments described herein have been directed to electrosurgical instruments with smoke evacuation features, the present disclosure is not intended to be so limited. Rather, the present disclosure is broadly directed to any hand-held instrument that includes fluid (e.g., liquids, gases, vapors, smoke, or combinations thereof) evacuation or delivery features as described herein. By way of non-limiting example, such hand-held instruments may include dental instruments (e.g., drills, polishing tools, scalers, compressed air tools, suction tools, irrigation tools, carries detection tools, water flossing tool (e.g., waterpik)), soldering tools (e.g., heated tools, smoke collection tools, desoldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical plasma hand pieces, argon beam surgical hand pieces, surgical laser hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hand-held instrument, comprising:
a hand piece having a proximal end, a distal end, and an interior conduit;
a front piece coupled to or integrated with the hand piece in a stationary position relative to the hand piece, the front piece having a distal opening leading into the interior conduit of the hand piece, the distal opening having an inner surface with a first dimension;
an extendable section at least partially disposed within the interior conduit of the hand piece and extending distally out of the distal opening of the front piece, the extendable section being configured for selective translation relative to the hand piece between a fully retracted position and a fully extended position, the extendable section having an outer surface with a second dimension, the second dimension being smaller than the first dimension such that a gap is formed between at least a portion of the inner surface of the distal opening in the front piece and the outer surface of the extendable section, the extendable section having a distally facing opening leading into an extendable section conduit; and
a negative pressure source configured to be in fluid communication with an atmosphere exterior of the hand-held instrument simultaneously through both the distal opening in the front piece via the interior conduit and the distally facing opening in the extendable section conduit via the extendable section conduit, the negative pressure source enabling:
the extendable section to function as a first fluid evacuation component, such that fluid can be drawn into the distally facing opening of the extendable section and through the extendable section conduit via the negative pressure source;

the gap and the interior conduit to function as a second fluid evacuation component, such that fluid can be drawn into the gap and through the interior conduit via the negative pressure source, wherein the gap is open directly to an atmosphere exterior of the hand piece such that fluid can be drawn into the interior conduit directly through the gap without the fluid passing through the extendable section conduit, wherein selective translation of the extendable section relative to the hand piece varies a distance between the first fluid evacuation component and the second fluid evacuation component.

2. The hand-held instrument of claim 1, further comprising an electrode tip disposed at a distal end of the extendable section, the electrode tip configured to transmit electrical energy to target tissue.

3. The hand-held instrument of claim 1, wherein the extendable section is selectively translatable along an axis extending from the proximal end to the distal end of the hand piece.

4. The hand-held instrument of claim 1, wherein the negative pressure source is a vacuum hose attached to the hand piece, the vacuum hose being configured to convey away fluid drawn into one or both of the interior conduit and the extendable section conduit.

5. The hand-held instrument of claim 4, wherein the vacuum hose is part of a utility conduit, and the utility conduit is coupled to the hand piece.

6. The hand-held instrument of claim 5, wherein the utility conduit is coupled to the hand piece at a utility conduit coupler disposed at or near the proximal end of the hand piece.

7. The hand-held instrument of claim 1, further comprising a utility conduit coupled to the hand piece and configured to connect a power cable and a vacuum hose to the electrosurgical instrument.

8. The hand-held instrument of claim 1, wherein the extendable section is formed from a conductive material.

9. The hand-held instrument of claim 1, wherein the front piece is formed with a tapered profile that tapers inwardly in a distal direction.

10. The hand-held instrument of claim 1, wherein the front piece includes one or more supports configured to hold or stabilize the extendable section in position relative to the front piece.

11. The hand-held instrument of claim 10, wherein the one or more supports are configured to frictionally maintain the position of the extendable section during operation of the hand-held instrument while allowing selective translation of the extendable section upon hand- applied force.

12. The hand-held instrument of claim 10, wherein the one or more supports are formed as inwardly extending radial extensions.

13. The hand-held instrument of claim 1, wherein the interior conduit is configured in size and shape to enclose the portions of the extendable section not extending distally beyond the hand piece.

14. The hand-held instrument of claim 1, wherein the front piece is disposed at the distal end of the hand piece.

15. The hand-held instrument of claim 1, further comprising a back stop configured to limit proximal translation of the extendable section within the interior conduit, and a front stop configured to limit distal movement of the extendable section within the interior conduit.

16. The hand-held instrument of claim 1, further comprising a connector joined to or integrated with the extendable section at a proximal end of the extendable section, the connector including one or more projections extending radially outwardly to an interior wall of the interior conduit and being configured to maintain the position of the extendable section relative to the interior conduit through friction.

17. The hand-held instrument of claim 16, wherein the connector is configured to frictionally maintain the position of the extendable section during operation of the hand-held instrument while allowing selective translation and rotation of the extendable section upon hand- applied force.

18. The hand-held instrument of claim 1, wherein the extendable section is formed with a length about the same length of the hand piece.

19. A hand-held instrument, comprising:
a hand piece having a proximal end and a distal end;
a first fluid evacuation component configured to be selectively translatable relative to the hand piece between a fully retracted position and a fully extended position, the first fluid evacuation component including a first conduit having a proximal opening and a distal opening, the first conduit extending distally from the hand piece and extending at least partially into the interior of the hand piece, wherein, via a negative pressure source, the first conduit is configured to direct fluid captured through the distal opening into the hand piece through the proximal opening; and
a second fluid evacuation component having a stationary positional relationship with the hand piece, the second fluid evacuation component including a second conduit having a distal opening in fluid communication with an atmosphere exterior of the hand-held instrument, the second conduit extending into the interior of the hand piece, wherein, via the negative pressure source, the second conduit is configured to direct fluid captured through the distal opening of the second conduit into the hand piece, the second conduit extending at least partially between the hand piece and the first fluid evacuation component, the distal opening of the second conduit being completely closed off to the atmosphere exterior of the hand-held instrument only when the first fluid evacuation component is selectively translated to the fully extended position thereby preventing fluid evacuation through the second fluid evacuation component.

20. The hand-held instrument of claim 19, wherein closing off the distal opening of the second conduit is configured to increase a negative pressure at the distal opening of the first conduit of the first fluid evacuation device. component.

21. The hand-held instrument of claim 19, wherein the first fluid evacuation component extends further distally than the second fluid evacuation component.

22. The hand-held instrument of claim 19, wherein the distal opening of the first conduit has a diameter that is smaller than a diameter of the distal opening of the second conduit.

23. The hand-held instrument of claim 22, wherein a ratio of the diameter of the distal opening of the second conduit to the diameter of the distal opening of the first conduit ranges from 1.1:1 to 10:1.

24. The hand-held instrument of claim 22, wherein a ratio of the diameter of the distal opening of the second conduit to the diameter of the distal opening of the first conduit ranges from 2:1 to 3:1.

25. The hand-held instrument of claim 19, further comprising an electrode tip coupled to a distal end of the first conduit, the electrode tip being configured to provide electrical energy to a target tissue.

26. The hand-held instrument of claim 19, further comprising a utility conduit coupled to the hand piece near the proximal end of the hand piece and configured to provide negative pressure to the first and second conduits to draw captured fluid through the first and second conduits and into the utility conduit.

27. An electrosurgical instrument, comprising:

an electrode tip configured to provide electrical energy to a target tissue;

a first smoke evacuation component having a stationary positional relationship with the electrode tip, the first smoke evacuation component including a first conduit with a distal opening in which the electrode tip is at least partially disposed, the first conduit extending proximally from the electrode tip to direct smoke captured through the distal opening away from the electrode tip;

a second smoke evacuation component configured to be selectively translatable relative to the electrode tip, the second smoke evacuation component including a second conduit with a distal opening in fluid communication with an atmosphere exterior of the hand-held instrument, the second conduit extending proximally from the electrode tip to direct smoke captured through the distal opening of the second conduit away from the electrode tip, wherein selective translation of the second smoke evacuation component relative to the electrode tip varies a distance between the first smoke evacuation component and the second smoke evacuation component; and a utility conduit comprising a negative pressure source in simultaneous communication with both the first and second smoke evacuation components and configured to provide negative pressure to both the first and second smoke evacuation components to draw captured smoke into the first and second smoke evacuation components, through the first and second conduits and into the utility conduit.

28. The electrosurgical instrument of claim 27, further comprising a hand piece having a proximal end and a distal end, the hand piece encasing at least proximal portions of the first and second conduits and being coupled to the utility conduit near the proximal end of the hand piece.

29. The electrosurgical instrument of claim 27, wherein the distal opening of the first conduit has a diameter that is smaller than a diameter of the distal opening of the second conduit.

30. The electrosurgical instrument of claim 27, wherein a ratio of a diameter of the distal opening of the second conduit to a diameter of the distal opening of the first conduit ranges from 1.1:1 to 10:1.

31. The electrosurgical instrument of claim 27, wherein a ratio of a diameter of the distal opening of the second conduit to a diameter of the distal opening of the first conduit ranges from 2:1 to 3:1.

\* \* \* \* \*